(12) United States Patent
Cobabe et al.

(10) Patent No.: US 7,614,107 B2
(45) Date of Patent: Nov. 10, 2009

(54) CLEANING APPARATUS WITH RECIPROCATING BRUSH HEAD

(75) Inventors: Aaron D. Cobabe, Syracuse, UT (US); David O. Meyers, Kaysville, UT (US); Darrell E. Goff, Highland, UT (US); W. Kenneth Thiess, Parker, CO (US); Qi-Chun Jackson Zhao, Shan Wei (CN)

(73) Assignee: SonicScrubbers, LLC, Layton, UT (US)

( * ) Notice: Subject to any disclaimer, the term of this patent is extended or adjusted under 35 U.S.C. 154(b) by 0 days.

(21) Appl. No.: 12/106,965

(22) Filed: Apr. 21, 2008

(65) Prior Publication Data
US 2008/0222822 A1 Sep. 18, 2008

Related U.S. Application Data

(63) Continuation of application No. 11/013,935, filed on Dec. 15, 2004, now Pat. No. 7,360,269.

(60) Provisional application No. 60/534,010, filed on Jan. 2, 2004.

(51) Int. Cl.
A46B 13/02 (2006.01)
(52) U.S. Cl. .............................. 15/28; 15/22.4; 15/22.1
(58) Field of Classification Search ................. 15/22.1, 15/22.2, 28, 22.4, 21.1
See application file for complete search history.

(56) References Cited

U.S. PATENT DOCUMENTS

| | | |
|---|---|---|
| 2,778,043 A | 1/1957 | Arf |
| 2,911,660 A | 11/1959 | Klemas et al. |
| 3,274,631 A | 9/1966 | Spohr |
| 3,667,454 A | 6/1972 | Prince |
| 3,699,952 A | 10/1972 | Waters et al. |
| 3,864,779 A | 2/1975 | Thomas |
| 4,137,588 A | 2/1979 | Sandt et al. |
| 4,654,921 A | 4/1987 | Dinner |
| 4,827,552 A | 5/1989 | Bojar et al. |
| 5,160,194 A | 11/1992 | Feldman |
| 5,341,534 A | 8/1994 | Serbinski et al. |
| 5,435,032 A | 7/1995 | McDougall |
| 5,465,444 A | 11/1995 | Bigler et al. |

(Continued)

FOREIGN PATENT DOCUMENTS

DE 43 15 320 A1 11/1994

OTHER PUBLICATIONS

Office Action dated May 16, 2005 issued in U.S. Appl. No. 11/014,626.

(Continued)

*Primary Examiner*—Laura C Guidotti
(74) *Attorney, Agent, or Firm*—Workman Nydegger

(57) ABSTRACT

A cleaning apparatus includes an elongated housing bounding a chamber with a motor disposed therein. A drive shaft is at least partially disposed within the chamber of the housing, the drive shaft being coupled with the motor such that during selective operation of the motor the drive shaft is rotated continuously. A head assembly includes an elongated head housing having a head drive shaft and a brush head mounted thereon. The head assembly is adapted to be selectively coupled with the body assembly so that the body drive shaft is coupled with the head drive shaft.

19 Claims, 13 Drawing Sheets

U.S. PATENT DOCUMENTS

| | | | |
|---|---|---|---|
| 5,467,495 | A | 11/1995 | Boland et al. |
| 5,504,959 | A | 4/1996 | Yukawa et al. |
| 5,577,285 | A | 11/1996 | Drossler |
| 5,590,434 | A | 1/1997 | Imai |
| 5,617,601 | A | 4/1997 | McDougall |
| 5,617,603 | A | 4/1997 | Mei |
| 5,625,916 | A | 5/1997 | McDougall |
| 5,652,990 | A | 8/1997 | Driesen et al. |
| 5,930,860 | A | 8/1999 | Shipp |
| 5,950,268 | A | 9/1999 | Murphy et al. |
| 5,956,792 | A | 9/1999 | Gutelius et al. |
| 5,974,615 | A | 11/1999 | Schwarz-Hartmann et al. |
| 6,021,538 | A * | 2/2000 | Kressner et al. ............ 15/28 |
| 6,092,252 | A | 7/2000 | Fischer et al. |
| 6,178,579 | B1 | 1/2001 | Blaustein et al. |
| 6,199,242 | B1 | 3/2001 | Masterman et al. |
| 6,253,405 | B1 | 7/2001 | Gutelius et al. |
| 6,347,425 | B1 * | 2/2002 | Fattori et al. ............ 15/22.1 |
| 6,363,565 | B1 | 4/2002 | Paffrath |
| 6,421,865 | B1 | 7/2002 | McDougall |
| 6,421,866 | B1 | 7/2002 | McDougall |
| 6,442,785 | B1 | 9/2002 | Robinson |
| 6,581,233 | B1 | 6/2003 | Cheng |
| 6,993,803 | B2 | 2/2006 | Chan |
| 7,258,229 | B2 | 8/2007 | Chan |
| 7,469,703 | B2 | 12/2008 | France et al. |
| 2001/0042280 | A1 | 11/2001 | Moskovich et al. |
| 2002/0004964 | A1 | 1/2002 | Luchino et al. |
| 2002/0039720 | A1 * | 4/2002 | Marx et al. ............ 433/216 |
| 2002/0066147 | A1 | 6/2002 | Schutz |
| 2003/0131427 | A1 | 7/2003 | Hilscher et al. |
| 2003/0140437 | A1 | 7/2003 | Eliav et al. |
| 2003/0154567 | A1 | 8/2003 | Drossler et al. |
| 2003/0163881 | A1 | 9/2003 | Driesen et al. |
| 2003/0221269 | A1 | 12/2003 | Zhuan |
| 2004/0083567 | A1 | 5/2004 | Lies |
| 2004/0200016 | A1 | 10/2004 | Chan et al. |
| 2005/0011023 | A1 | 1/2005 | Chan |
| 2005/0053895 | A1 | 3/2005 | Pinyayev et al. |
| 2005/0066996 | A1 | 3/2005 | France et al. |

OTHER PUBLICATIONS

Office Action dated Jan. 10, 2006 issued in U.S. Appl. No. 11/014,626.
Office Action dated Sep. 6, 2006 issued in U.S. Appl. No. 11/014,626.
Office Action dated Apr. 30, 2007 issued in U.S. Appl. No. 11/014,626.
Office Action dated Nov. 20, 2007 issued in U.S. Appl. No. 11/014,626.
Office Action dated May 15, 2005 issued in U.S. Appl. No. 11/013,935.
Office Action dated Dec. 30, 2005 issued in U.S. Appl. No. 11/013,935.
Office Action dated Aug. 17, 2006 issued in U.S. Appl. No. 11/013,935.
Office Action dated Apr. 18, 2007 issued in U.S. Appl. No. 11/013,935.
Notice of Allowability dated issued in U.S. Appl. No. 11/013,935.

* cited by examiner

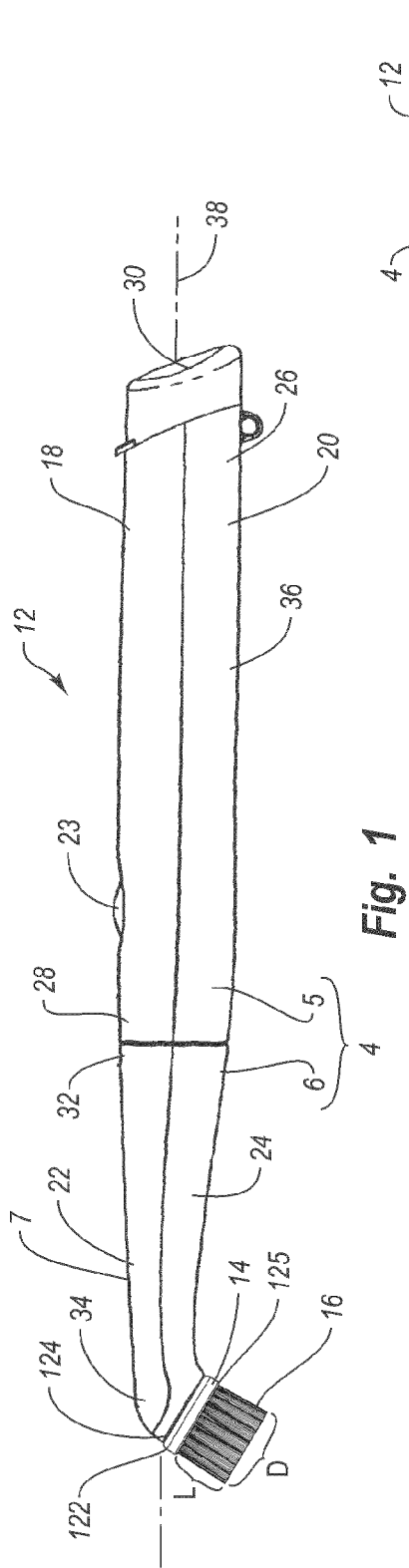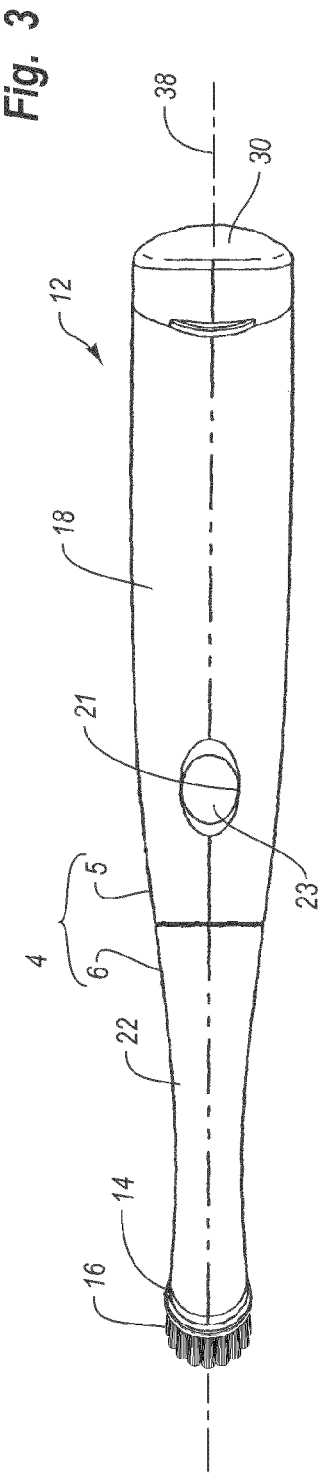
Fig. 1
Fig. 2
Fig. 3

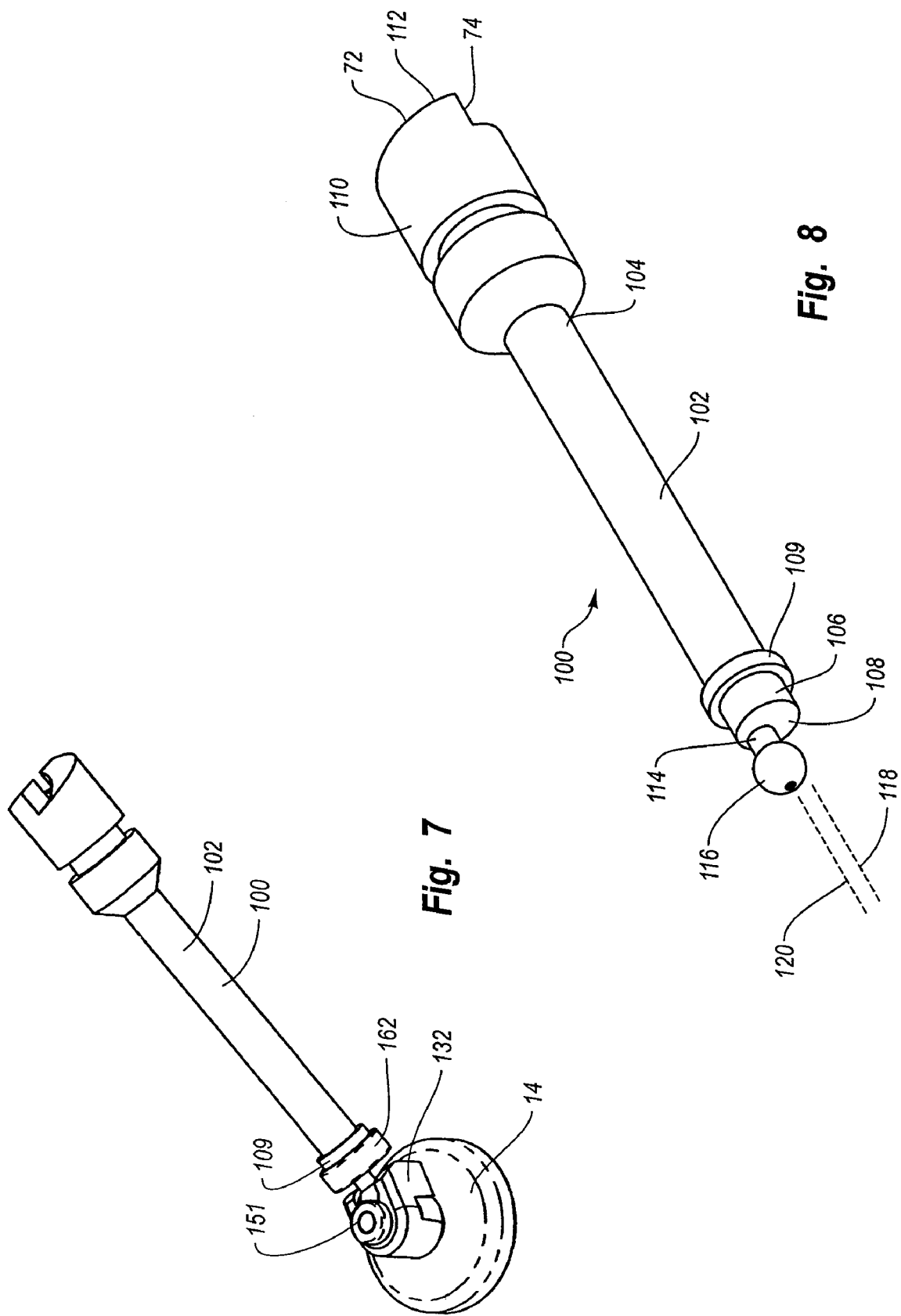

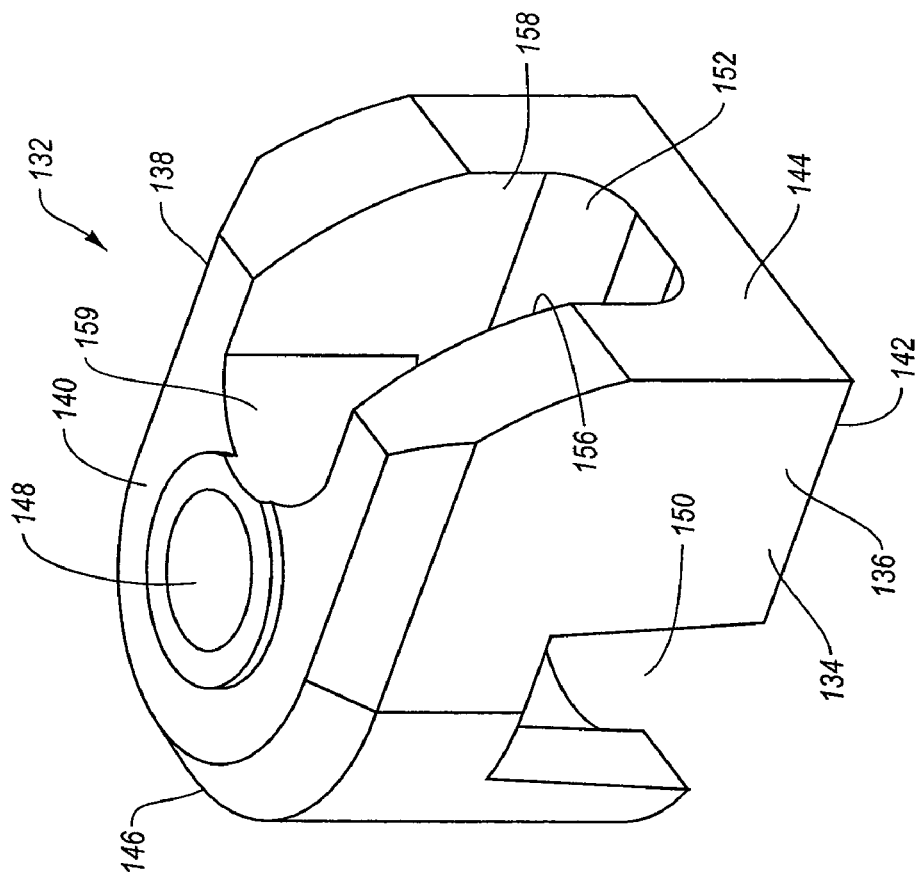
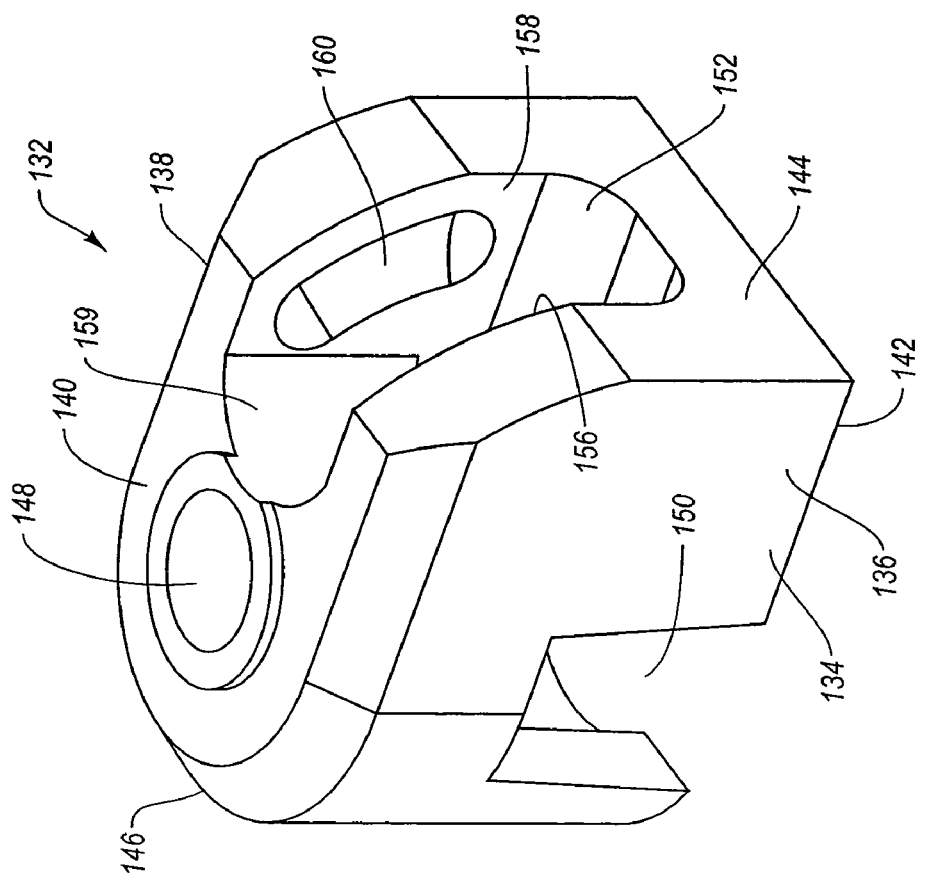

US 7,614,107 B2

CLEANING APPARATUS WITH RECIPROCATING BRUSH HEAD

CROSS-REFERENCE TO RELATED APPLICATIONS

This application is a continuation application of application Ser. No. 11/013,935, filed Dec. 15, 2004, which claims priority to U.S. Provisional Application Ser. No. 60/534,010, filed Jan. 2, 2004 which applications are incorporated herein by specific reference.

BACKGROUND OF THE INVENTION

1. The Field of the Invention

The present invention relates to hand held cleaning apparatus having a reciprocating or rotating brush head.

2. The Relevant Technology

Household cleaning is a never ending business. Although there are numerous types of sponges and brushes that are specially designed to clean large, open surface areas such as countertops, sinks, and bathtubs, there are fewer resources available for cleaning the difficult cracks, corners, and other hard to reach areas that are ubiquitous in a home. Although conventional sponges and brushes can certainly be used for cleaning corners and other hard to reach areas, the configuration and large size of such conventional cleaners makes them difficult to access such areas. The user is often required to apply extensive force by the ends or tips of the fingers so as to force the cleaner into the crack or corner to be cleaned. Such cleaning is tiring and often results in cramping of the hand and/or fingers.

This problem is compounded by the fact that corners and cracks are typically where dirt, mold, soap scum, and other undesirables tend to grow or build-up. As such, extra energy or force is often necessary to clean such locations.

Conventional toothbrushes are often used to clean such hard to reach areas. The problem with toothbrushes, however, is that because they are specifically designed for cleaning teeth around sensitive gums, toothbrushes are typically too soft and do not have a good angle for any extended, aggressive scrubbing of hard surfaces. Furthermore, because of the small handles on toothbrushes, any significant scrubbing using a toothbrush again produces fatigue and cramping of the hand.

Accordingly, what is needed are improved cleaning apparatus which can be used for cleaning small, hard to reach areas, which can be used for durable, extended scrubbing, and which can be used with minimal fatigue.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 1 is a an elevated side view of one embodiment of the inventive cleaning apparatus;

FIG. 2 is a top plan view of the cleaning apparatus shown in FIG. 1;

FIG. 3 is an elevated front end view of the cleaning apparatus shown in FIG. 1;

FIG. 7 is a perspective view of a subassembly of the cleaning apparatus shown in FIG. 1 showing a drive shaft coupled with a hub and brush head;

FIG. 8 is an enlarged perspective view of the drive shaft shown in FIG. 7;

FIG. 9A is an enlarged perspective view of the hub shown in FIG. 7;

FIG. 9B is an enlarged perspective view of an alternative embodiment of the hub shown in FIG. 9A;

DETAILED DESCRIPTION OF THE PREFERRED EMBODIMENTS

Figure 4:
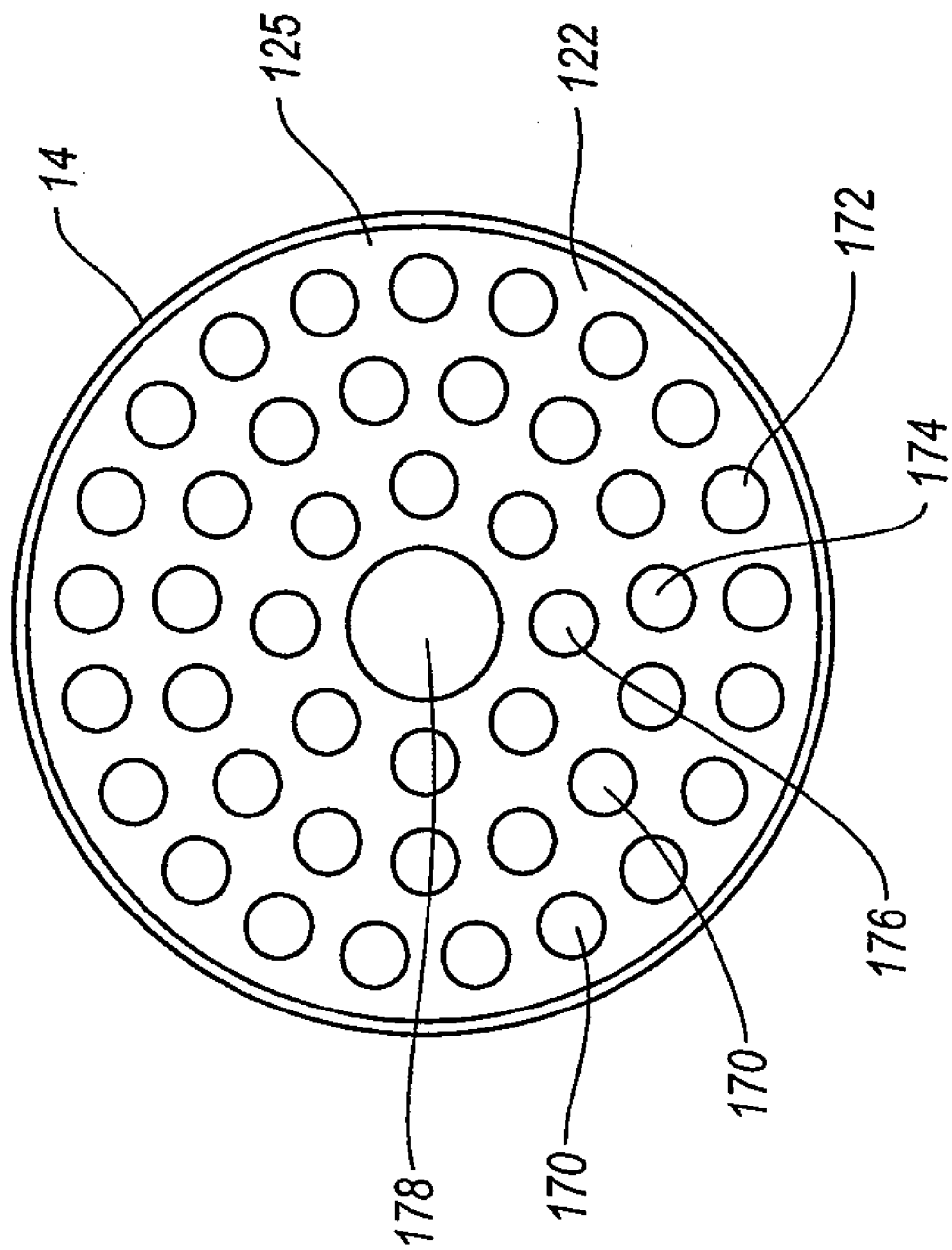
FIG. 4 is an elevated front view of the front face of the brush head shown in FIG. 3.

The present invention relates to cleaning apparatus having a reciprocating or rotating brush head. The cleaning apparatus is generally designed for domestic use in cleaning small, hard to reach areas such as cracks, corners, grooves and crevices. For example, the cleaning apparatus can be used for cleaning corners and around faucets on counter tops and in showers. It can also be used for spot scrubbing materials such as fabric and carpets. It is appreciated, however, that the apparatus can be used for cleaning any type of surface in commercial, residential, or any other application. The cleaning apparatus, however, is not designed for use as a toothbrush.

Depicted in FIGS. 1-3 is one embodiment of a cleaning apparatus 4 incorporating features of the present invention. Cleaning apparatus 4 generally comprises a body assembly 5 having a removable head assembly 6. Head assembly 6 includes a head housing 7 having an upper head housing 22 which mates with a lower head housing 24. Each of head housings 22 and 24 extend between a proximal end 32 and an opposing distal end 34.

Head assembly 6 further includes a rotatable brush head 14 having a brush 16 mounted thereon. As will be discussed below in greater detail, brush head 14 comprises an annular carrier plate 122 having a top surface 124 and an opposing bottom surface 125. Depicted in FIG. 4, a plurality of tufting holes 170 are formed on bottom surface 125. In one embodiment tufting holes 170 are circular and each have a diameter in a range between about 1 mm to about 4 mm with about 2 mm to about 3 mm being more common. Tufting holes 170 are shown disposed in concentric rings. Alternatively, tufting holes 170 can also be randomly disposed or be in other patterns.

In the embodiment depicted, tufting holes 170 from an outer ring 172, a middle ring 174, an inner ring 176 and a center tufting hole 178. As seen in FIG. 3, disposed within each tufting hole 170 is a tuft 180 which is comprised of a plurality of bristles 182. The combined tufts 180 form brush 16. Bristles 182 can be made of a variety of different materials having different lengths and diameters. By adjusting the properties of the bristles 182, brush 16 can be formed having different stiffnesses to better suit different uses. In general, bristles having shorter length and increased diameter have increased stiffness.

Bristles 182 can be made from a variety of different natural or synthetic materials. In one embodiment, bristles 182 are comprised of a polymer material such as nylon. In other embodiments, such as for use in cleaning a barbeque grill, bristles 182 can be comprised of a metal such as brass, stainless steel, or copper. As depicted in FIG. 1, each bristle has an exposed length L which is typically in a range between about 0.3 cm to about 2.5 cm with about 1 cm to about 2 cm being more common. The depicted brush 16 has a substantially cylindrical configuration with a maximum diameter D that is typically in a range between about 1 cm to about 5 cm, with about 1 cm to about 3 cm being common, and about 1.5 cm to about 2.5 cm being more common. Larger brushes may have a diameter in a range from about 3 cm to about 5 cm. In alternative embodiments, brush 16 can have any desired configuration and can have any desired dimensions, including longer lengths and diameters, so as to function for a particular purpose.

Because head assembly 6 is removable from body assembly 5, it is appreciated that a variety of different head assemblies 6 can be made, each having a brush 16 of different configuration and/or properties. For example head assembly 6 can be formed each having a brush 16 with soft bristles, medium bristles, stiff bristles or combinations thereof. In one embodiment the soft bristles are comprised of a polymeric material having a diameter in a range between about 0.15 mm to about 0.25 mm with about 0.18 mm to about 0.23 mm being more common. Medium polymeric bristles typically have a diameter in a range between about 0.30 mm to about 0.48 mm with about 0.37 mm to about 0.42 mm being more common. Finally, polymeric stiff bristles typically have a diameter in a range between about 0.48 mm to about 0.75 mm with about 0.52 mm to about 0.58 mm being more common. By way of comparison, bristles on tooth brushes typically have a diameter less than 0.15 mm so that the bristles are not so stiff as to damage the gums or enamel of the teeth.

In one embodiment having a combination of bristles 182, tufting holes 170 in outer ring 172, middle ring 174, and inner ring 176 (FIG. 4) are filled with medium bristles while center tufting hole 178 is filled with stiff bristles forming a stopping tuft. The bristles in the stopping tuft are shorter than the other bristles. During use, the stiffness of the stopping tuft helps limit the collapse of the other tufts as the brush is pressed against the surface to be cleaned. This helps to ensure that the tips of the bristles, as opposed to the sides, are primarily used for scrubbing. Bristles having different properties can also be defined by relative percentages. For example, in a brush having a stopping tuft and cleaning tufts, the bristles of the cleaning tufts can have a length that is at least 20% longer or at least 30% longer than the bristles of the stopping tuft and a diameter that is at least 30% smaller or at least 40% smaller than the bristles of the stopping tuft.

Similarly, in one embodiment depicted in FIG. 3, brush 16 can comprise a group of central tufts 8 which are surrounded by outer perimeter tufts 9. The outer perimeter tufts 9 are slightly longer and softer than central tufts 8. As such, light contact by brush 16 produces soft scrubbing by outer perimeter tufts 9 while harder biasing of brush 16 causes central tufts 8 to engage the surface, thereby producing harder scrubbing. In alternative embodiments, all the tufts/bristles can be the same length, diameter, or stiffness or any combination of lengths, diameters and stiffness can be used.

Body assembly 5 includes a body housing 12 having a substantially cylindrical configuration. Body housing 12 can have a circular, elliptical or any other desired transverse cross section and is sized to comfortably fit within the hand of a user. In one embodiment, body housing 12 has a maximum diameter in a range between about 2.5 cm to about 4.5 cm. Other dimensions can also be used. Body housing 12 comprises an upper body housing 18 which mates with a lower body housing 20. Each of body housings 18 and 20 also extend from a proximal end 26 to an opposing distal end 28. Upper body housing 18 has an aperture 21 in which a flexible button 23 is mounted (see FIG. 5). Removably mounted to proximal end 26 of body housing 12 is an end cap 30. It is noted that button 23 is positioned on one side of cleaning apparatus 4 while brush 16 projects from the other side of cleaning apparatus 4. This configuration enables the user to easily activate button 23 during using of cleaning apparatus 4. Furthermore, by having this configuration, the force used to press down on button 23, such as with the thumb of the user, can also be used for pressing the brush against the surface to be cleaned.

Head housing 7, body housing 12, and end cap 30 combine to form a housing 36. Housing 36 has a substantially cylindrical configuration with a length extending between proximal end 32 and end cap 30 that is typically in a range between about 15 cm to about 35 cm with about 20 cm to about 30 cm being more common. Other dimensions can also be used. In alternative embodiments housing 36 can have a variety of other configurations. Although housing 36 may not be completely symmetrical along its entire length, housing 36 has a substantially central longitudinal axis 38 extending therethrough.

Figure 5:
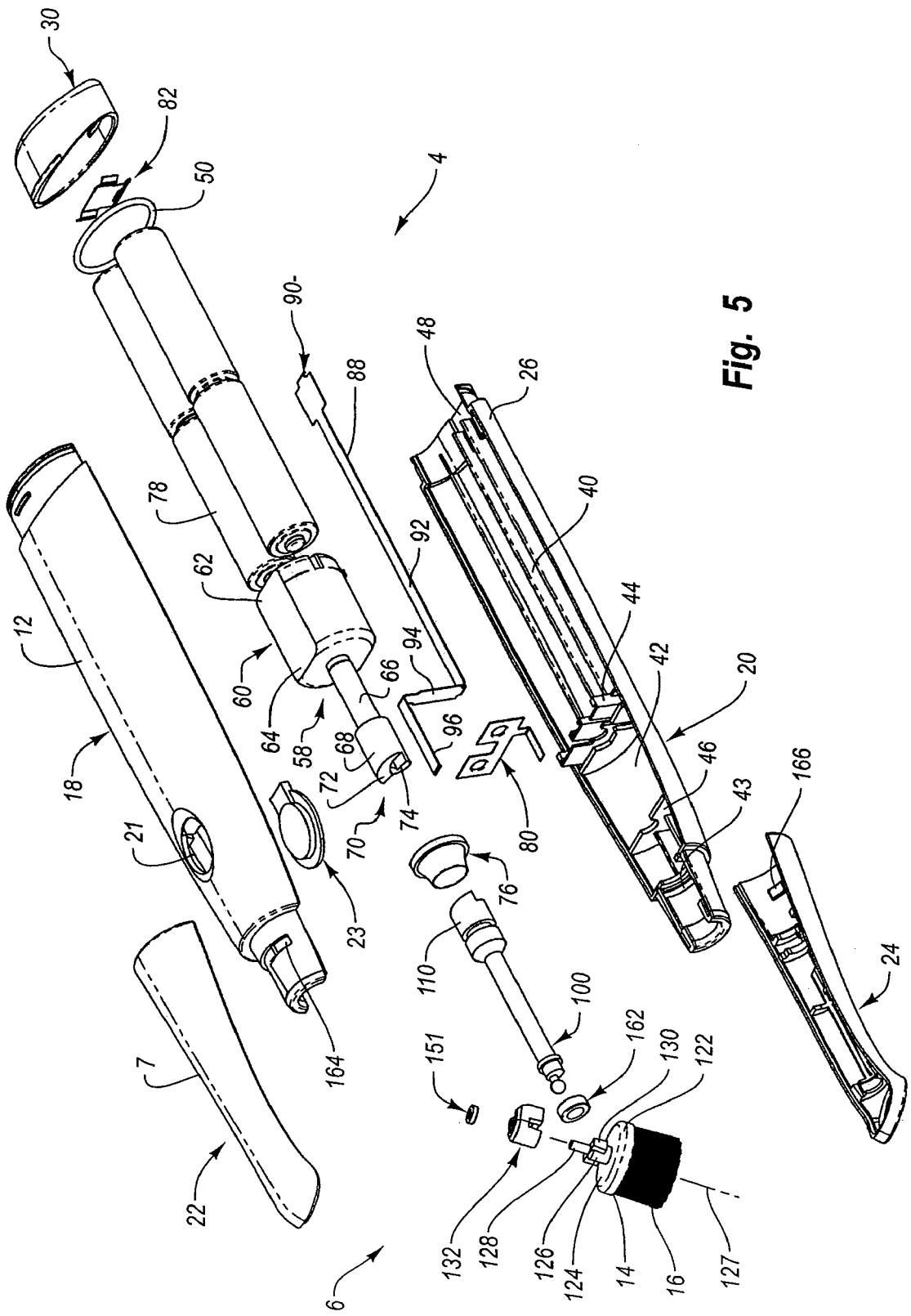
FIG. 5 is an exploded view of the cleaning apparatus shown in FIG. 1.

As depicted in FIG. 5, body housing 12 bounds a battery compartment 40, a motor compartment 42, and a shaft compartment 43. A partition 44 is formed between compartment 40 and 42 while a partition 46 is formed between compartment 42 and 43. Battery compartment 40 is accessed through an opening 48 formed at proximal end 26 of body housing 12. Opening 48 is selectively closed by end camp 30. An annular seal ring 50 forms a liquid tight seal between body housing 12 and end cap 30.

Figure 6:
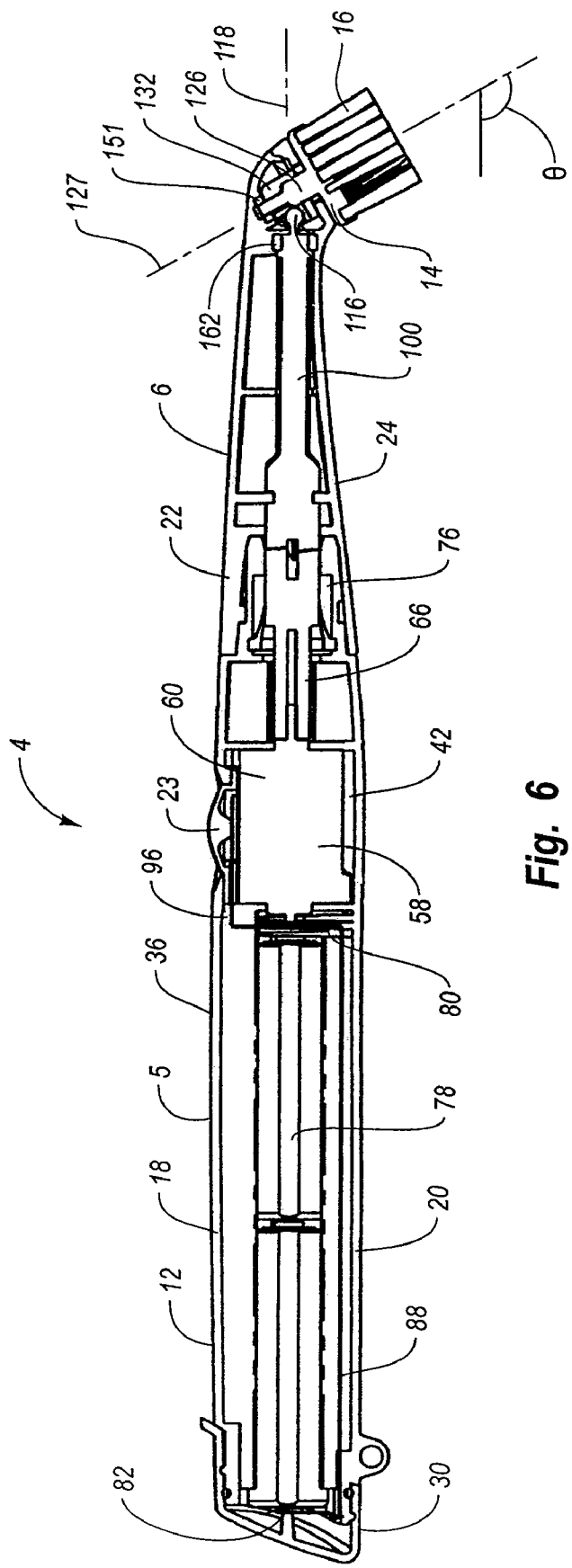
FIG. 6 is a cross sectional side view of the cleaning apparatus shown in FIG. 1.

As depicted in FIGS. 5 and 6, cleaning apparatus 4 further includes a motor assembly 58. Motor assembly 58 comprises a motor 60 having a proximal end 62 and an opposing distal end 64 that is mounted within motor compartment 42. Projecting from distal end 64 of motor 60 into shaft compartment 43 is a drive shaft 66 terminating at a first coupling 68. First coupling 68 terminates at an end face 70. End face 70 comprises a pair of sloping surfaces 72 that are connected by stepped shoulders 74. An annular shaft seal 76 encircles first coupling 68 and forms a liquid tight seal between first coupling 68 and body housing 12.

Battery compartment 40 is configured to receive a plurality of batteries. For example, in the embodiment battery compartment 40 is configured to receive four batteries 78 of a size AA. Other sizes and numbers of batteries can also be used in alternative embodiments. The positive end of batteries 78 bias against a first contact plate 80 which is in electrical communication with motor 60. The negative end of batteries 78 bias against a second contact plate 82 which is mounted within end cap 30.

An elongated switch 88 has a first end 90 which is in electrical communication with second contact plate 82 when end cap 30 is mounted to body housing 12. Switch 88 comprises an elongated base 92 which extends along battery compartment 40, a riser 94 which extends along partition 44, and a flexible lever arm 96 which projects so as to be disposed between button 23 and motor 60. When button 23 is manually depressed, lever 96 is biased against motor 60, thereby closing the circuit which is energized by batteries 78. In turn, as the circuit is closed, the energy from batteries 78 causes motor 60 to rotatably drive drive shaft 66. As button 23 is released, the circuit is broken and motor 60 is turned off. In alternative embodiments, it is appreciated that a variety of different switching mechanisms can be used so that motor 60 can be continually activated without having to continually manually depress button 23. Furthermore, it is appreciated that batteries 78 can be replaced with an electrical cord.

With further reference to FIGS. 5 and 6, head assembly 6 further comprises a drive shaft 100. As depicted in FIG. 8, drive shaft 100 comprises an elongated shaft 102 having a proximal end 104 and an opposing distal end 106. Distal end 106 terminates at a distal end face 108. Radially encircling and outwardly projecting from shaft 102 at distal end 106 is an annular flange 109. A bearing or bushing 162 (FIG. 7) is mounted on shaft 102 so as to bias against flange 109. Mounted at proximal end 104 of shaft 102 is a second coupling 110 having an end face 112 that is complementary to end face 70 of first coupling 68. That is, second coupling 110 is configured to mesh with first coupling 68 so that stepped shoulders 74 bias against one another. As a result, rotation of drive shaft 66 by motor 60 is transferred through couplings 68 and 110 to cause rotation of shaft 102.

Extending from end face 108 at distal end 106 of shaft 102 is a stem 114. Mounted on the end of stem 114 is a rounded head 116. In the embodiment depicted, head 116 is spherical or substantially spherical. Here it is noted, as will be discussed below in greater detail, shaft 102 has a rotational axis and central longitudinal axis 118, which in the depicted embodiment are the same, and stem 114 has a central longitudinal axis 120. Stem 114 is eccentrically mounted on end face 108 of shaft 102 so that central longitudinal axis 120 of stem 114 is offset from central longitudinal axis 118 of shaft 102. Rotational axis 118 can also be the same axis as the rotational axis and central longitudinal axis of drive shaft 66 and can also be the same as central longitudinal axis 38 of housing 36 (FIG. 1).

Returning to FIG. 5, brush head 14 comprises annular carrier plate 122, as previously discussed, having top surface 124. Projecting from top surface 124 is a spindle 126. Spindle 126 comprises a central axle 128 having an arm 130 projecting from each side thereof. A rotational axis 127, about which brush 16 and brush head 14 rotate, extends through spindle 126. Rotational axis 127 can also be the central axis for brush 16 and brush head 14. Mounted on spindle 126 is a hub 132. As depicted in FIG. 9A, hub 132 has opposing side surfaces 136 and 138 which extend between a top surface 140 and an opposing bottom surface 142. Hub 132 also includes a front face 144 and an opposing back face 146. A passage 148 extends from top surface 140 to bottom surface 142. A side channel 150 extends through side surfaces 136 and 138 adjacent to bottom surface 142 so as to intersect with passage 148.

During assembly, hub 132 is received over spindle 126 so that axle 128 extends through passage 148 and arms 130 are received within side channel 150. A bearing or bushing 151 (FIG. 5) is mounted on axle 128 at top surface 140 of hub 132. In this configuration, hub 132 is engaged with spindle 126 such that rotation of hub 132 facilitates rotation of spindle 126 and thus the remainder of brush head 14. In alternative embodiment, it is appreciated that hub 132 can be integrally formed with brush head 14.

Hub 132 further comprises a channel 152 formed on front face 144 and extending to top surface 140. Channel 152 is vertically aligned with passage 148 and is bounded by a first engagement surface 156, a spaced apart second engagement surface 158, and an inside face 159 extending therebetween. Engagement surfaces 156 and 158 are opposingly facing and are in substantially parallel alignment. Recessed along each engagement surface 156 and 158 is a locking channel 160. Each locking channel 160 is elongated and is slightly arched along the length thereof. The distance between engagement surfaces 156 and 158 of hub 132 is smaller than the diameter of rounded head 116.

Figure 10:
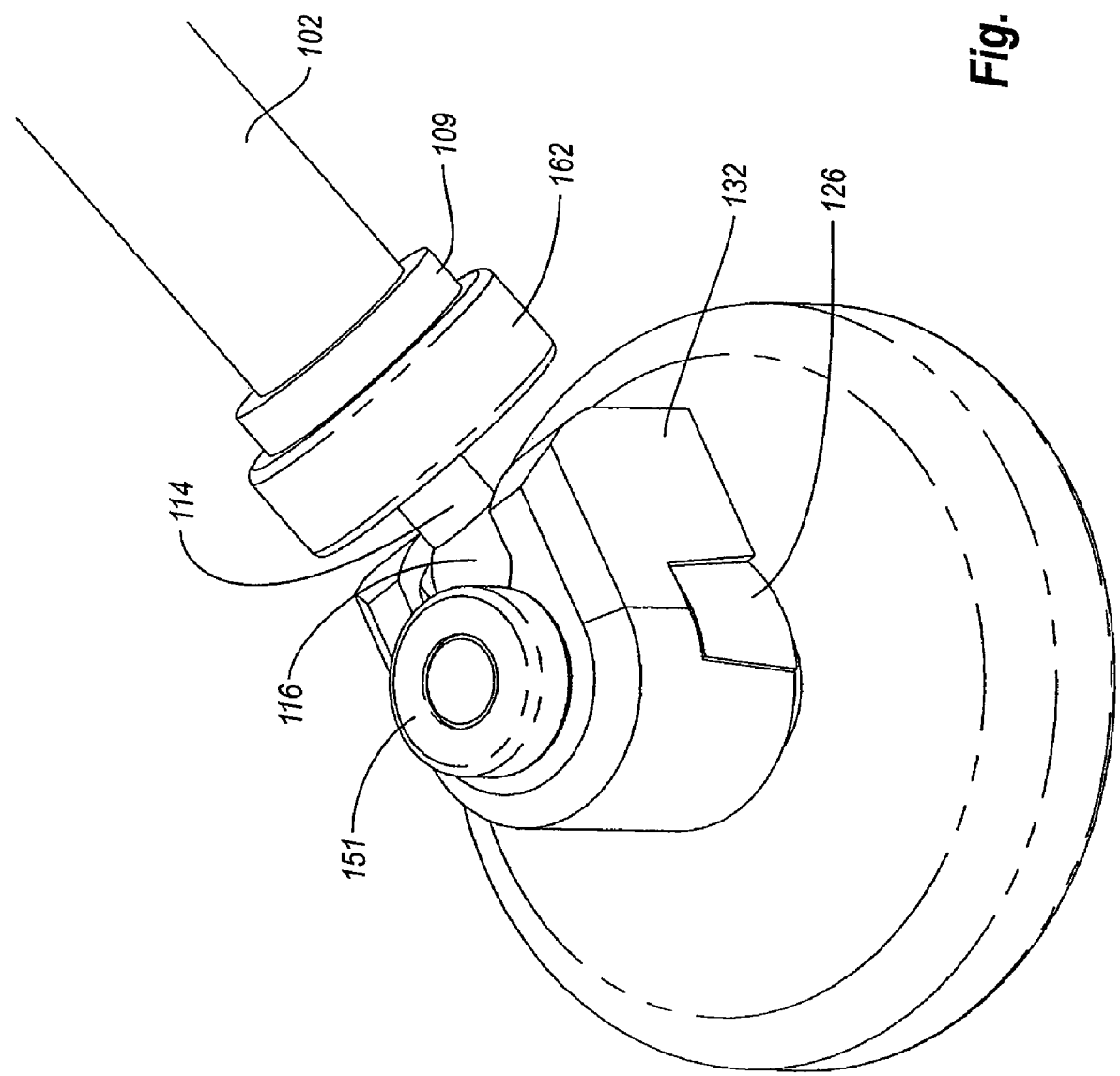
FIG. 10 is an enlarged perspective view of the coupled parts shown in FIG. 7.

As depicted in FIGS. 7 and 10, however, hub 132 is configured so that head 116 can be snap-fit between engagement surfaces 156 and 158 so that head 116 is a resiliently captured within locking channels 160 formed on engagement surfaces 156 and 158. In this configuration, head 116 is resiliently biased between faces 156 and 158.

In an alternative embodiment depicted in FIG. 9B, locking channels 160 can be eliminated so that engagement surfaces 156 and 158 are substantially flat. In this embodiment, head 116 can be sized to snugly or loosely fit between engagement surfaces 156 and 158.

Returning to FIG. 5, head housing 7 is enclosed over drive shaft 100 and hub 132 so that head housing 7 rides against bearings 151 and 162. Bayonet slots 164 are formed on distal end 28 of body housing 12 while bayonet prongs 166 project from proximal end 32 of head housing 7. As such, head assembly 6 can be removably connected to body assembly 5 using the bayonet connection (FIG. 1).

In the above assembled configuration, couplings 68 and 110 are mated. Accordingly, as button 23 is depressed, motor 60 is energized causing drive shaft 66 and drive shaft 100 to each rotate about their rotational or central longitudinal axis. In turn, because stem 114 and rounded head 116 are mounted eccentrically on shaft 102, head 116 rotates in a circle. That is, as shaft 102 spins or rotates, head 116 begins to rotate in an enlarged circle so as to bias against engagement surface 158 of hub 132 causing hub 132 with connected brush head 14 and brush 16 to rotate in a first direction about axle 128. The length and arch of locking channels 160 allows for free rotation of head 116 within locking channels 160.

Once head 116 has moved to its furthest extent in one direction, head 116 then begins to bias against the opposing engagement surface 156 causing hub 132, with connected brush head 14 and brush 16, to rotate in the opposing direction about axle 128. As such, rapid rotation of drive shaft 100 with head 116 causes hub 132 with connected brush head 14 and brush 16 to rapidly reciprocate. By securing head 116 within locking channels 160, a snug engagement can be formed between hub 132 and head 116. This snug fit optimizes the transfer of movement between drive rod 100 and hub 132. That is, the snug fit eliminates slop between hub 132 and drive shaft 100 even after head 116 has begun to wear within locking channels 160.

Once cleaning apparatus 4 is energized, brush 16 can be biased against a surface for cleaning. It is noted that brush 16 is positioned at an orientation relative housing 36 so as to optimize convenience and use. For example, with reference to FIG. 6, in one embodiment brush 16 projects relative to the central longitudinal axis of body assembly 5 or head assembly 6 so as to form a set inside angle θ therewith typically in a range between about 90° to about 180° with about 110° to about 140° being more common. Other angles can also be used. Expressed in other terms, rotational axis 127 of brush head 14 or brush 16 intersects with rotational axis 38 of the drive shaft or of central longitudinal axis 118 of housing 36 so as to form the set inside angle θ as discussed above. By having the angle θ at about 110° to about 140°, the user is able to more conveniently place and use brush 16 while holding onto housing 36.

The present invention may be embodied in other specific forms without departing from its spirit or essential characteristics. The described embodiments are to be considered in all respects only as illustrative and not restrictive. For example, it is appreciated that locking channels 160 need not merely be recessed within inner side walls 156 and 158 but can completely extend through hub 132. Furthermore, it is not necessary that head 116 be spherical. In alternative embodiments, it is appreciated that head 116 can be elliptical or have a variety of other configurations that mate with complementary locking channels.

Figure 11:
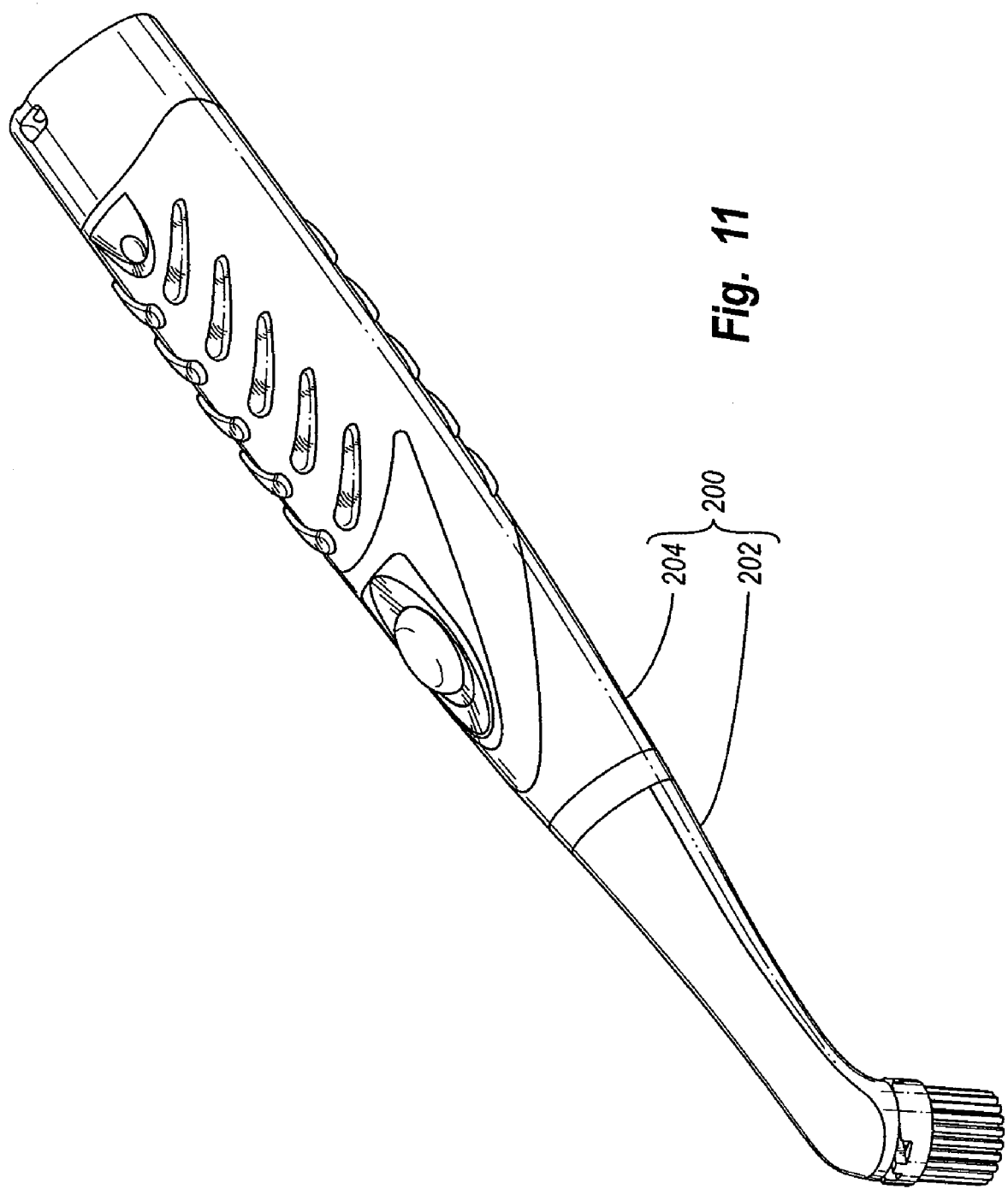
FIG. 11 is a perspective view of an alternative embodiment of a cleaning apparatus.
Figure 12A:
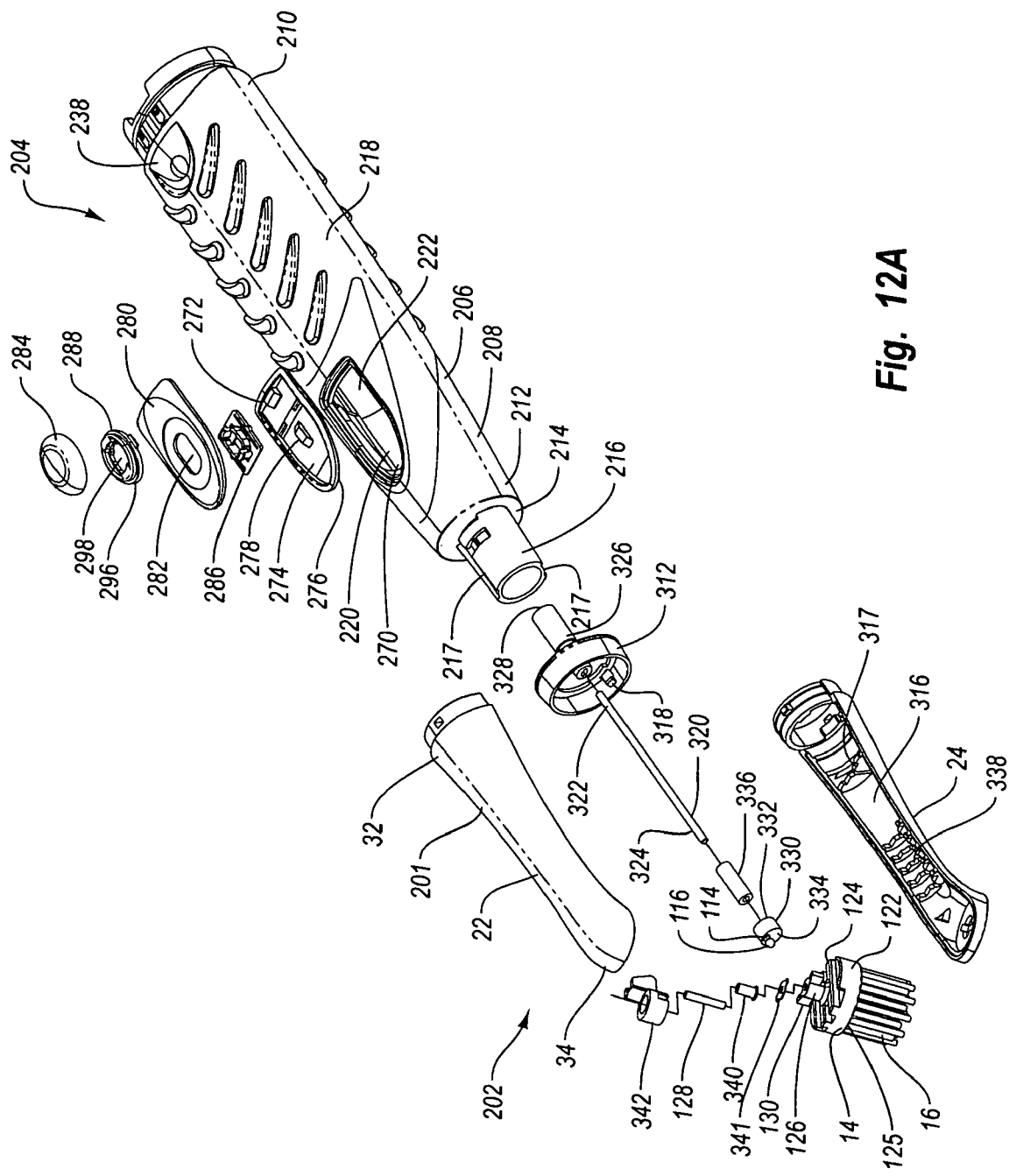
FIG. 12A and 12B are exploded views of the cleaning apparatus shown in FIG. 11.

Depicted in FIG. 11 is an alternative embodiment of a cleaning apparatus 200 incorporating features of the present invention. Like elements between cleaning apparatus 4 and 200 are identified by like reference characters. Cleaning apparatus comprises a head assembly 202 and a body assembly 204. Turning to FIG. 12A, body assembly 204 comprises a body housing 206 which is molded as a tubular member. Body housing 206 comprises a handle portion 208 having a proximal end 210 and an opposing distal end 212. Distal end 212 terminates at and end face 214 from which a tapered, tubular stem 216 projects. A pair of opposing bayonet slots 217 are formed along stem 216. Handle portion 208 and stem 216 are typically comprised of a substantially rigid plastic such as ABS. An overlay 218, comprised of a softer, flexible plastic such as TPE or rubber, is molded over a section of handle portion 208. Overlay 218 allows improved gripping of cleaning apparatus 200.

Figure 12B:
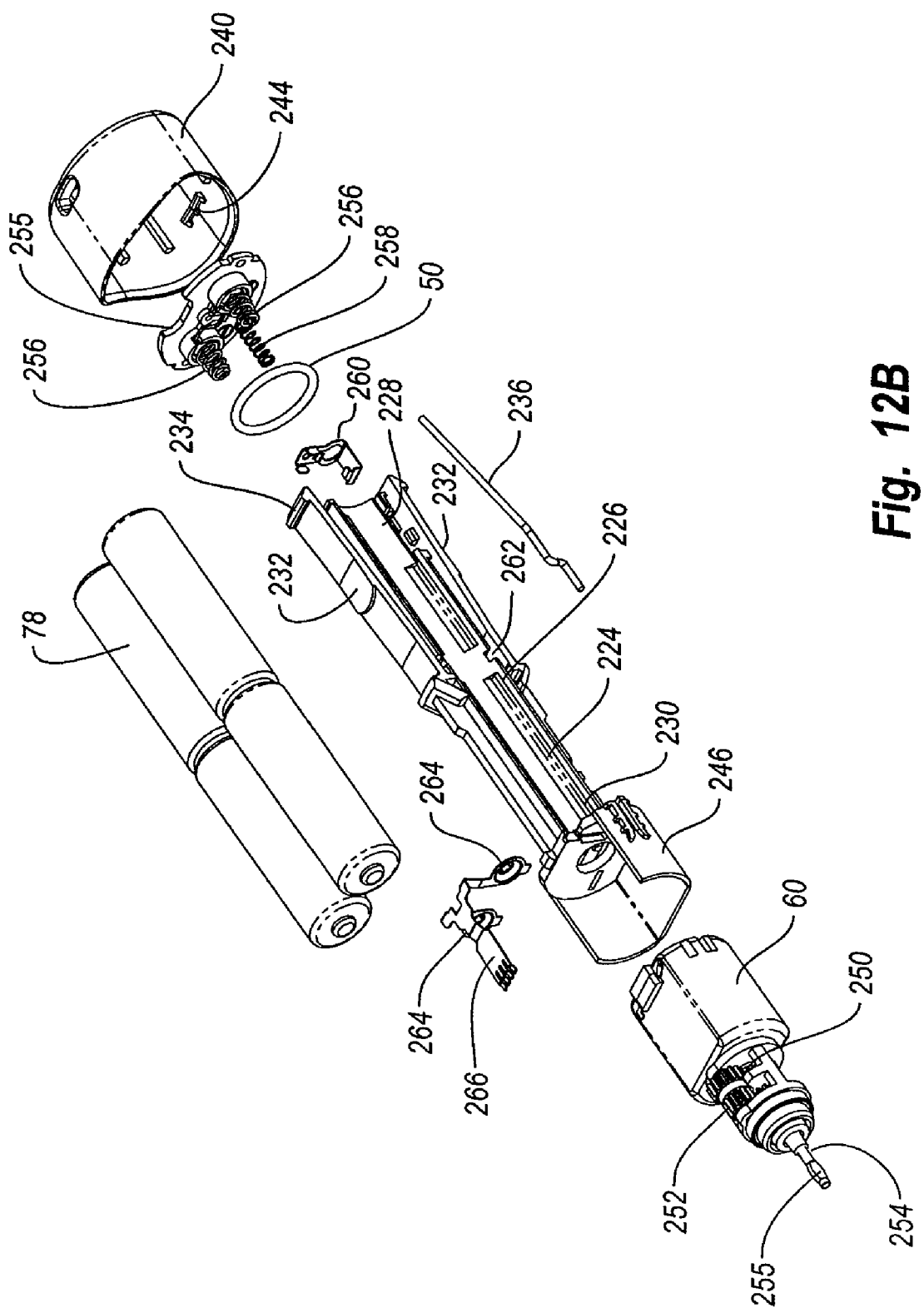
Figure 13:
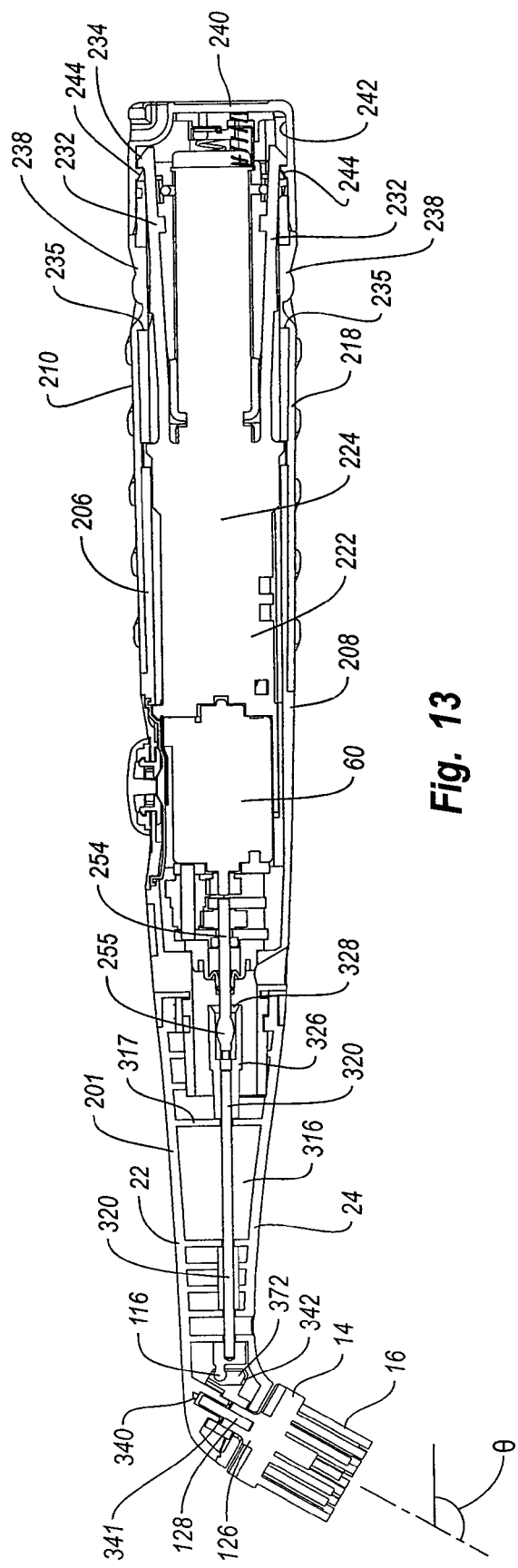
FIG. 13 is a cross sectional side view of the cleaning apparatus shown in FIG. 11.

Body housing 206 has an interior surface 220 which bounds a chamber 222. Turning to FIG. 12B, secured within chamber 222 is a guide 224. Guide 224 comprises an elongated partition wall 226 having a proximal end 228 and an opposing distal end 230. The sides of partition wall 226 are curved so that batteries 78 can be complementary received on each side thereof. A cantilevered latch 232 is formed at proximal end 228 at both the top and bottom of partition wall 226. Each latch 232 terminates at a barb 234. A spring 236 is positioned between partition wall 226 and each latch 232 so that each latch 232 can be selectively compressed toward partition wall 226 and, when released, each latch 232 resiliently rebounds. As depicted in FIG. 13, holes 235 are formed through each side of handle portion 208 at proximal end 210. An engaging portion 238 of overlay 218 is molded over holes 235. Guide 224 is positioned within chamber 222 so that each latch 232 is aligned with a corresponding hole 235. A user is thus able to manually press inward on the flexible engaging portions 238 of overlay 218 so as to selectively inwardly press latches 232.

Latches 232 are used for securing an end cap 240 to proximal end 210 of body housing 206. Specifically, end cap 240 has an interior surface 242 with a pair of opposing catches 244 formed thereon. When end cap 240 is pushed onto proximal end 210 of body housing 206, barbs 234 on latches 232 engage catches 244 so as to securely lock end cap 240 on body housing 206. To remove end cap 240, engaging portions 238 are manually depressed as discussed above so as to inwardly flex latches 232 and thus release barbs 234 from catches 244.

Returning to FIG. 12B, cupped support 246 is formed at distal end 230 of partition wall 226 and is used to support motor 60. Motor 60 rotates an initial shaft 250 which in turn rotates a drive shaft 254. Drive shaft 254 has a head 255 formed at a distal end thereof. Head 255 typically has a non-circular transverse cross section such that it can engage with a coupler as discussed below in greater detail. In the embodiment depicted, head 255 comprises a flattened portion of drive shaft 254. In alternative embodiments, head 255 can have any number of different polygonal or non-circular transverse cross sections.

A conventional gear assembly 252 extends between initial shaft 250 and drive shaft 254 so that the torque produced by drive shaft 254 is adjusted relative to the torque produced by initial shaft 250 by a ratio in a range between about 1.5:1 to about 3.5:1. Increasing the torque capacity of drive shaft 254 enables brush 16 to continue to reciprocate or rotate even when substantial bearing force is applied to brush 16 while scrubbing. This is contrary to many conventional electric toothbrushes where it is desired that the brush stop moving or significantly slow when too much force is applied so that the toothbrush does not damage the gums.

It is appreciated that there are a variety of different mechanism that can be used to transfer electricity from batteries 78 to motor 60. In the illustrated embodiment, the four batteries 78 are disposed in parallel. The negative end of the back two batteries 78 bias against a corresponding spring 256 which are each in electrical communication with a transfer spring 258. The springs are mounted on a plate 255 which is secured within end cap 240. Transfer spring 258 biases against a contact 260. An electrical lead 262 extends from contact 260 to motor 60. The positive end of the front two batteries 78 bias against a corresponding contact 264 which are each in electrical communication with a flexible switch 266. Switch 266 is positioned above motor 60 such that when switch 266 is biased against motor 60, the circuit is complete and motor 60 is energized.

In an alternative embodiment, batteries 78 can be positioned in series rather then parallel. In this embodiment, springs 258 are in electrical communication with each other but transfer spring 256, contact 260, and lead 262 are eliminated. Likewise, the two contacts 264 are separated from each other. One of contacts 264 is in direct electrical communication with motor 60 while the other contact 264 remains connected with switch 266. Placing batteries 78 in series increases the voltage to provide more power to the motor.

Turning to FIG. 12A, an opening 270 is formed on a top surface body housing 206 so as to communicate with chamber 222. Opening 270 is aligned with motor 60 and switch 266. Secured within opening 270 is a flexible diaphragm 272. Diaphragm 272 has a top surface 274 and an opposing bottom surface 276. A projection 278 is formed on top surface 274. A cover plate 280 has an elongated hole 282 extending therethrough and is secured over opening 270 so that hole 282 is aligned with projection 278. A button 284 is slidably mounted to cover plate 280 by a catch 286 and a retainer 288.

Figures 14A, 14B, 14C:
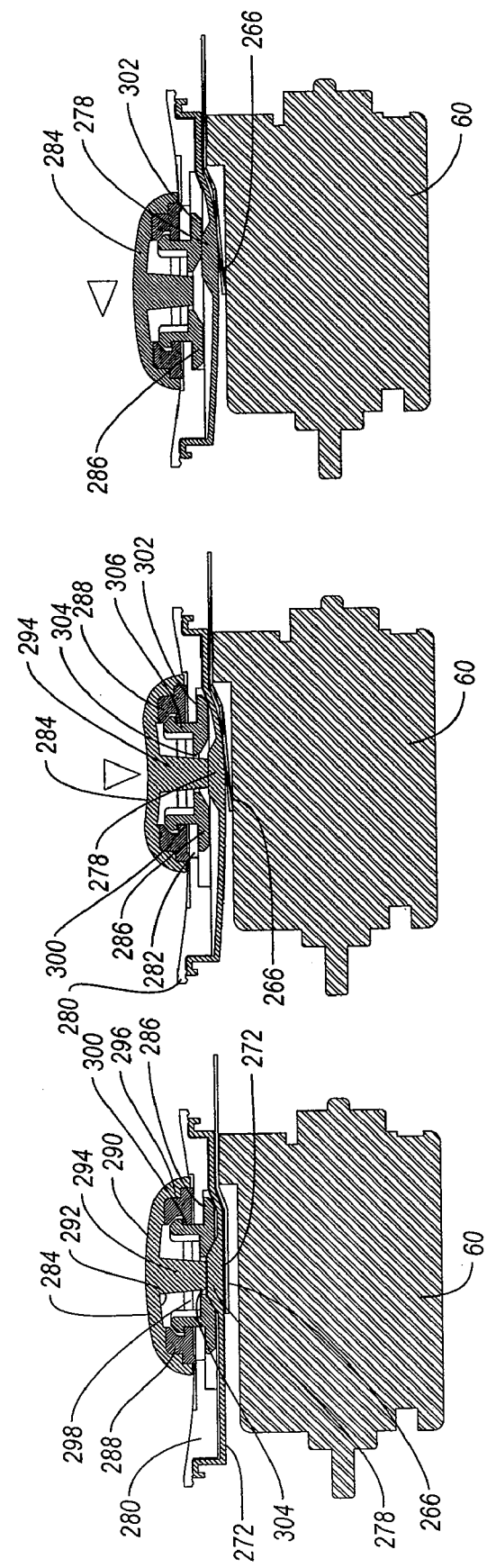
FIG. 14A is an enlarged cross sectional side view of the button switch assembly shown in FIG. 13 in an off position.
FIG. 14B is an enlarged cross sectional side view of the button switch assembly shown in FIG. 14A in a momentary position.
FIG. 14C is an enlarged cross sectional side view of the button switch assembly shown in FIG. 14A in an open position.

As depicted in FIG. 14A, button 284 comprises a generally cup-shaped body 290 having an interior surface 292 with a stem 294 projecting therefrom. Button 284 is comprised of a resiliently flexible material which is typically a natural or synthetic rubber. Retainer 288 comprises a substantially circular frame 296 having an opening 298 extending therethrough. Opening 298 is at least partially bounded by a lip 300. Retainer 288 is comprised of a substantially rigid material or at least a material that is more rigid than the material used for button 284. Button 284 is secured to retainer 288 so that stem 294 passes through opening 298. In one embodiment, button 284 is secured to retainer 288 by being molded directly onto retainer 288 during the formation of button 284, i.e., overlay molding process.

Catch 286 (FIG. 14B) comprises a base 302 having an opening 304 extending therethrough. A pair of barbed prongs 306 upwardly project from a top surface of base 302 on opposing sides of opening 304. Catch 286 is used to secure button 284 on cover plate 280. Specifically, button 284 and retainer 288 are positioned on the top surface of cover plate 280 so that stem 294 is aligned with opening 282 of cover plate 280. Prongs 306 of catch 286 are then pushed up through opening 282 of cover plate 280 from the bottom surface thereof so that prongs engage with lip 300 of retainer 288 by a snap fit connection.

In this assembled configuration, button 284 can selectively side on cover plate 280 between an off position as shown in FIG. 14A and an on position as shown in FIG. 14C. In the off position, projection 278 of diaphragm 272 is disposed between stem 294 of button 284 and switch 266 and is at least partially disposed within opening 304 of catch 286. In this position, switch 266 is spaced apart from motor 60 so that no electrical contact is made. From the off position, there are two ways in which a user can energize motor 60. In one approach, as depicted in FIG. 14B, a user can simply press down on the center of button 284. In so doing, stem 294 is pressed down against projection 278 which in turn pushes down switch 266 so that switch 266 contacts motor 60, thereby energizing motor 60. When the user releases button 284, button 284 resiliently returns to the off position.

In the second approach as depicted in FIG. 14C, the user manually slides button 284 along cover plate 280. In so doing, base 302 of catch 286 rides over projection 278 which pushes projection 278 downward again causing switch 266 to contact motor 60, thereby energizing motor 60. Motor 60 remains energized until button 284 is again moved back to the off position. The button assembly thus enables a single, integral button to activate the motor in two different modes of operation.

Returning to FIG. 12A, head assembly 202 comprises a head housing 201 which includes upper head housing 22 and lower head housing 24 each having proximal end 32 and opposing distal end 34. Head housing 201 bounds a channel 316 extending along the length thereof which is at least partially divided by complementary partition walls 317 formed on housing 22 and 24. Secured between housing 22 and 24 at proximal end 32 is an engagement ring 312. Engagement ring 312 has opposing bayonet prong 318 formed on an interior surface thereof. Head assembly 202 is removably secured to body assembly 204 by inserting stem 216 of body housing 206 within proximal end 32 of head assembly 202 so that bayonet prongs 318 are received within bayonet slots 217 and then rotating head assembly 202 relative to body assembly 204.

Head assembly 202 comprises a drive shaft 320 having a proximal end 322 and an opposing distal end 324. Proximal end 322 has a coupler 326 secured thereto. Coupler 326 has a socket 328 formed on the free end thereof that is designed to removably engage with head 255 on drive shaft 254 extending from motor 60. Specifically, socket 328 has a configuration complementary to head 255 such that when head 255 is received within socket 328, rotation of drive shaft 254 causes rotation of drive shaft 320. Head 255 is removably received within socket 328 when head assembly 202 is removably coupled with body assembly 204 as discussed above.

An enlarged disk 330 is secured to distal end 324 of drive shaft 320. In the embodiment depicted, disk 330 has a substantially cylindrical configuration that includes a proximal end face 332 and an opposing distal end face 334. Distal end 324 of drive shaft 320 is centrally secured to proximal end face 332. In contrast, stem 114 and rounded head 116 are mounted on distal end face 334 at a location spaced radially outward from the rotational axis of drive shaft 320. That is, stem 114 is eccentrically mounted on end face 334 in the same manner as discussed above with regard to cleaning apparatus 4.

It is noted that centrally positioning enlarged disk 330 at the end of drive shaft 320 helps to stabilize drive shaft 320 during the rotation of eccentrically mounted rounded head 116. In alternative embodiments, however, drive shaft 320 can have the same diameter as disk 330 or disk 330 can be eliminated and an arm formed between drive shaft 320 and stem 114. Other conventional techniques can also be used to eccentrically position rounded head 116. A cylindrical bushing 336 encircles drive shaft 320 toward distal end 324 and is supported within supports 338 formed on the interior surface of head housing 201.

As with cleaning apparatus 4, cleaning apparatus 200 includes brush head 14. Brush head 14 comprises carrier plate 122 having bottom surface 125 with brush 16 comprised of bristles formed thereon. Plate 122 also has top surface 124 with spindle 126 and arms 130 projecting therefrom. Axle 128 centrally projects from spindle 126 and has a rotational axis extending therethrough. A tubular bushing 340 is secured to upper head housing 22 and encircles axle 128 (FIG. 13). Axle 128 and spindle 126 are received within a hub 342 with a wear plate 341 positioned between bushing 340 and spindle 126.

Figure 15:
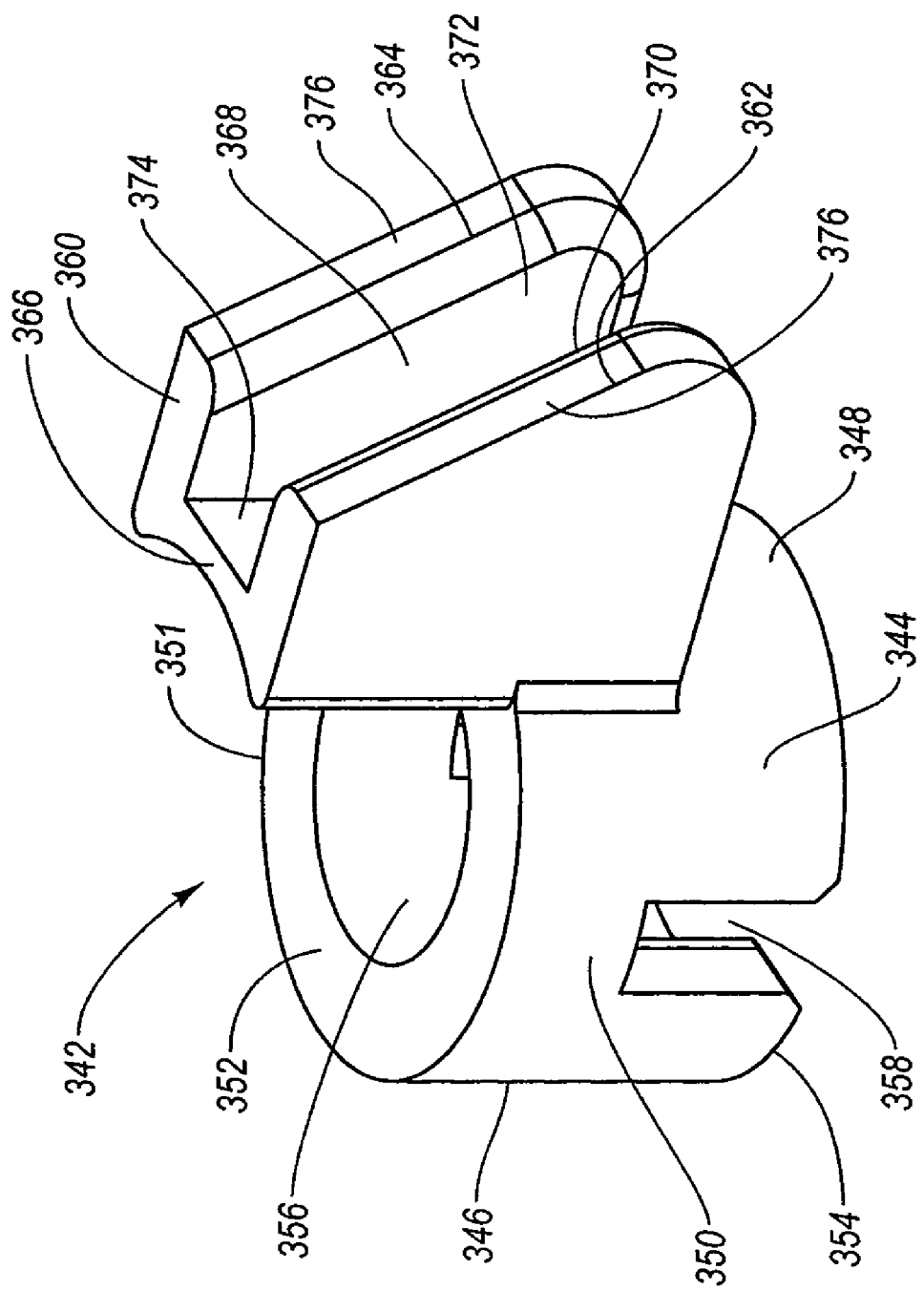
FIG. 15 is an enlarged perspective view of the hub shown in FIG. 12A.

As depicted in FIG. 15, hub 342 comprises a substantially cylindrical base 344 having a front face 346, a back face 348, and opposing side faces 350 and 351 which each extend between a top surface 352 and an opposing bottom surface 354. A passage 356 centrally extends through base 344 from top surface 352 to bottom surface 354. A side channel 358 extends through side surfaces 350 and 351 adjacent to bottom surface 354 so as to intersect with passage 356. Side channel 358 is configured so that when spindle 126 is received within passage 356, arms 130 are received within side channel 358 so that hub 342 is interlocked with brush head 14. Wear plate 341 also has tabs projecting from the side thereof which are received within side channel 358 of hub 342 so that wear plate 341 is secured to hub 342. In one embodiment where bushing 340 is metal and spindle 126 is plastic, wear plate 341 prevents bushing 340 from producing undue wear on spindle 126.

Projecting from back face 348 of base 344 is a guide 360. Guide 360 comprises a first side wall 362, a complementary spaced apart second side wall 364, and a back wall 366 extending therebetween. Guide 360 partially bounds a channel 368 that is vertically aligned with passage 356. Channel 368 is bounded by a first engagement surface 370, a spaced apart second engagement surface 372, and an inside face 374 extending therebetween. Engagement surfaces 370 and 372 are opposingly facing, are substantially flat, and are in substantially parallel alignment. The distance between engagement surfaces 370 and 372 of hub 342 is substantially equal to the diameter of rounded head 116.

Comparable to the embodiment depicted in FIG. 10 and as illustrated in FIG. 13, rounded head 116 is received within channel 368. As rounded head 116 is continuously rotated about the rotational axis of drive shaft 320 due to the rotation of drive shaft 254, rounded head 116 alternatingly pushes against opposing engagement surfaces 370 and 372 so as to cause hub 342, brush head 14, and brush 16 to reciprocate in a rotational pattern about the rotation axis extending through spindle 126.

As with cleaning apparatus 4, in cleaning apparatus 200 the rotational axis of drive shaft 320 intersects with the rotational axis of brush head 14 so as to form an inside angle θ that is typically greater than 95° and is more commonly in a range between about 110° to about 140°. As rounded head 116 travels in its circular pattern, rounded head 116 travels longitudinally along the length of side walls 362 and 364. Because of the above discussed angular orientation of brush head 14, rounded head 116 is disposed farther away from the rotational axis of brush head 14 when rounded head 116 is disposed at the bottom of side walls 362 and 364 and is closer to the rotational axis of brush head 14 when rounded head 116 is disposed at the top of side walls 362 and 364. Accordingly, to ensure that rounded head 116 is retained within channel 368 during its circular movement, side walls 362 and 364 are wider at the bottom than at the top.

In one embodiment rounded head 116 has a substantially spherical configuration. This design has a number of benefits. For example, in part because of the above discussed angular orientation of brush head 14, rounded head 116 contacts engagement surfaces 370 and 372 along a number of different points on rounded head 116 that are longitudinally spaced proximal to distal and top to bottom. By making rounded head 116 spherical, this helps to ensure continued minimal contact between rounded head 116 and engagement surfaces 370 and 372 so as to minimize wear.

Furthermore, due to tolerances in mounting brush head 14, on occasion as brush 16 is biased against a surface for cleaning, brush head 14 will tilt slightly causing the distal end of rounded head 116 to bias against inside face 374 of hub 342 (FIG. 15). This contact between rounded head 116 and inside face 374 helps to stabilize and reinforce brush head 14. By making rounded head 116 spherical, the contact surface between rounded head 116 and inside face 374 is minimized. It is also noted that both of side walls 362 and 364 terminate at an outside edge 376. These outside edges 376 are designed so that they can bias against distal end face 334 of disk 330 as brush head 14 is tilted during use so as to also help stabilize and reinforce brush head 14.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A cleaning apparatus comprising:
    (i) a body assembly comprising:
        an elongated body housing having a chamber;
        a motor at least partially disposed within the chamber of the body housing; and
        a body drive shaft at least partially disposed within the chamber of the body housing, the body drive shaft being coupled with the motor such that during selective operation of the motor, the body drive shaft is rotated continuously about a rotational axis thereof, and
    (ii) a head assembly comprising:
        an elongated head housing;
        a head drive shaft disposed within the head housing and having a rotational axis about which the head drive shaft rotates;
        a brush head comprising a carrier plate having a plurality of bristles secured thereon and having a rotational axis about which the brush head rotates, the brush head being mounted on the head housing and being coupled with the head drive shaft such that continuous rotation of the head drive shaft facilitates reciprocating rotation of the brush head, the rotational axis of the brush head intersecting the rotational axis of the head drive shaft so as to form an inside angle therebetween in a range between about 110° to about 140°, the inside angle remaining constant during reciprocating rotation of the brush head, the head assembly being adapted to be selectively coupled with the body assembly so that the body drive shaft is coupled with the head drive shaft.

2. The cleaning apparatus as recited in claim 1, wherein each bristle has a diameter greater than 0.30 mm.

3. The cleaning apparatus as recited in claim 2, wherein the carrier plate has a plurality of tufts mounted thereon, each of the plurality of tufts being comprised of the plurality of the bristles.

4. The cleaning apparatus as recited in claim 1, wherein each bristle has a diameter greater than 0.40 mm.

5. The cleaning apparatus as recited in claim 1, wherein the head housing terminates at a distal end face having a maximum diameter, the carrier plate being disposed directly adjacent to the distal end face of the head housing and having a maximum diameter that is larger than the maximum diameter of the distal end face of the head housing.

6. The cleaning apparatus as recited in claim 1, wherein the plurality of bristles combine to form a brush, the brush being substantially cylindrical and having a maximum diameter in a range between about 1 cm to about 4 cm.

7. The cleaning apparatus as recited in claim 1, further comprising an activation button position on a first side of the body housing, the brush head projecting form a second side of the body housing that is opposite of the first side.

8. The cleaning apparatus as recited in claim 1, wherein the head housing is removably coupled with the body housing by being selectively twisted onto the body housing.

9. The cleaning apparatus as recited in claim 1, wherein the plurality of bristles combine to form a brush, the brush being substantially cylindrical and having a maximum diameter in a range between about 3 cm to about 5 cm.

10. The cleaning apparatus as recited in claim 1, further comprising a gear assembly disposed between the motor and the body drive shaft, the gear assembly increasing the torque produced on the drive shaft by the motor by a ratio in a range between about 1.5:1 to about 3.5:1.

11. A cleaning system kit comprising:
    (i) a body assembly comprising:
        an elongated body housing having a chamber;
        a motor at least partially disposed within the chamber of the body housing; and
        a body drive shaft at least partially disposed within the chamber of the body housing, the body drive shaft being coupled with the motor such that during selective operation of the motor, the body drive shaft is rotated continuously about a rotational axis thereof;
    (ii) a first head assembly comprising:
        a first head housing;
        a first head drive shaft disposed within the first head housing and having a rotational axis about which the first head drive shaft rotates;
        a first brush head comprising a carrier plate having a plurality of bristles secured thereon and having a rotational axis about which the first brush head rotates, the first brush head being mounted on the first head housing and being coupled with the first head drive shaft such that continuous rotation of the first head drive shaft facilitates reciprocating rotation of the first brush head, the rotational axis of the first brush head intersecting the rotational axis of the first head drive shaft so as to form an inside angle therebetween in a range between about 110° to about 140°, the inside angle remaining constant during reciprocating rotation of the first brush head, the first head assembly being adapted to be selectively coupled with the body assembly so that the body drive shaft is coupled with the first head drive shaft; and (iii) a second head assembly comprising:

a second head housing;

a second head drive shaft disposed within the second head housing and having a rotational axis about which the second head drive shaft rotates;

a second brush head comprising a carrier plate having a plurality of bristles secured thereon, the second brush head having a rotational axis about which the second brush head rotates and having a configuration that is different than the first brush head, the second brush head being mounted on the second head housing and being coupled with the second head drive shaft such that continuous rotation of the second head drive shaft facilitates rotation of the second brush head, the rotational axis of the second brush head intersecting the rotational axis of the second head drive shaft so as to form an inside angle therebetween in a range between about 110° to about 140°, the inside angle remaining constant during reciprocating rotation of the second brush head, the second head assembly being adapted to be selectively coupled with the body assembly so that the body drive shaft is coupled with the second head drive shaft.

12. The cleaning system kit as recited in claim 11, wherein at least a portion of the bristles on the first brush head have different properties than the bristles on the second brush head.

13. The cleaning system kit as recited in claim 11, wherein at least a portion of the bristles on the first brush head have a different length than the bristles on the second brush head.

14. The cleaning system kit as recited in claim 11, wherein at least a portion of the bristles on the first brush head have a different diameter than the bristles on the second brush head.

15. The cleaning system kit as recited in claim 11, wherein the bristles on the first brush head combine to form a first brush having a first maximum diameter and the bristles on the second brush head combine to form a second brush having a second maximum diameter, the first maximum diameter being larger than the second maximum diameter.

16. The cleaning system kit as recited in claim 11, wherein at each bristle of the first head housing has a diameter greater than 0.30 mm.

17. The cleaning system kit as recited in claim 11, wherein each bristle of the first head housing has a diameter greater than 0.40 mm.

18. The cleaning system kit as recited in claim 11, wherein the plurality of bristles of the first brush head combine to form a brush, the brush being substantially cylindrical and having a maximum diameter in a range between about 1 cm to about 4 cm.

19. The cleaning system kit as recited in claim 11, wherein the first head housing is removably coupled with the body housing by being selectively twisted onto the body housing.

* * * * *

UNITED STATES PATENT AND TRADEMARK OFFICE
CERTIFICATE OF CORRECTION

| | | |
|---|---|---|
| PATENT NO. | : 7,614,107 B2 | Page 1 of 1 |
| APPLICATION NO. | : 12/106965 | |
| DATED | : November 10, 2009 | |
| INVENTOR(S) | : Cobabe et al. | |

It is certified that error appears in the above-identified patent and that said Letters Patent is hereby corrected as shown below:

Column 1
Line 57, delete "a"

Column 6
Line 15, delete "a"
Line 66, change "38" to --118--
Line 67, change "118" to --38--

Column 14
Line 17, delete "at"

Signed and Sealed this
Twenty-eighth Day of June, 2011

David J. Kappos
*Director of the United States Patent and Trademark Office*